United States Patent [19]
Arnaud et al.

[11] 3,966,555
[45] June 29, 1976

[54] ALPHA-GALACTOSIDASE PRODUCTION

[75] Inventors: Nichole Arnaud, Vendome, France; David Anthony Bush, Maidstone, England

[73] Assignee: Societe d'Assistance Technique pour Produits Nestle S.A., Lausanne, Switzerland

[22] Filed: Jan. 30, 1975

[21] Appl. No.: 545,356

[30] Foreign Application Priority Data

Feb. 1, 1974 Switzerland.......................... 1403/74

[52] U.S. Cl................................. 195/66 R; 195/81
[51] Int. Cl.²........................................ C07G 7/028
[58] Field of Search................ 195/66, 65, 81, 36 R

[56] References Cited
UNITED STATES PATENTS

| | | | |
|---|---|---|---|
| 3,674,644 | 7/1972 | Yokotsuka et al..................... | 195/65 |
| 3,795,585 | 3/1974 | Suzuki et al........................... | 195/65 |

*Primary Examiner*—Alvin E. Tanenholtz
*Attorney, Agent, or Firm*—Watson Leavenworth Kelton & Taggart

[57] ABSTRACT

A process for the production of α-galactosidase by culturing the mold *Penicillium duponti* in an aqueous medium containing at least one sugar with at least one αD-galactopyranosyl bond and collecting the mycelium thus obtained.

10 Claims, No Drawings

ALPHA-GALACTOSIDASE PRODUCTION

This invention relates to a process for the production of α-galactosidase by culturing a microorganism in a medium containing at least one sugar having at least one αD-galactopyranosyl bond.

It is known that α-galactosidase, an enzyme capable of hydrolysing oligosaccharides containing galactose, i.e. sugars with at least one αD-galactopyranosyl bond, in other words "flatulent" sugars such as stachyose and raffinose, may perform a significant commercial function, on the one hand in the production of foods based on leguminosae and on the other hand in the production of beet sugar.

Among the leguminosae, soya in particular is used in large quantities for feeding cattle and, to an increasing extent, is replacing all or some of the staple foods, such as meat and milk-based products, intended for human consumption. Most of the assimilation problems attributable to the presence of non-resorbable oligosaccharides responsible for flatulence may be resolved by treating the basic materials, such as defatted soya flour, with enzymatic preparations of microbial origin. Accordingly, it is known that, in order to make up for the absence of α-galactosidase in human beings and cattle, it is possible to use microorganisms capable of synthesising this specific enzyme.

The production of sucrose or saccharose from sugar beet is limited by the presence of raffinose which inhibits the normal crystallisation of saccharose. One conventional method of increasing the production yield of saccharose from sugar beet is to add to the juice or molasses of treated sugar beet α-galactosidase which decomposes the raffinose into saccharose and galactose. The yield is increased both by the elimination of the inhibiting effect of raffinose and by the decomposition product of the raffinose.

It is also known that microorganisms known for their ability to produce α-galactosidase, such as *Mortierella vinacea*, variety *raffinoseutilizer*, have their effect in producing α-galactosidase induced by the presence of a galacto-oligosaccharide, for example raffinose, or lactose in the fermentation medium. It is for this reason that various culture media have been proposed, ranging from a conventional basic medium enriched with raffinose to a medium consisting of soya powder, rice bran and water.

The present invention arose out of efforts to derive some benefit from effluents which are rich in nutritive materials favourable to the development of microorganisms and which, for this very reason, constitute a fairly significant pollution factor. One characteristic effluent in this respect is the water which has been used for blanching vegetables, especially haricot beans, before they are conserved. It has been found that the stachyose and raffinose present in blanching water of this kind induce the synthesis of an α-galactosidase during the growth of a thermophilic fungus in this water. It has also been found that this α-galactosidase is not accompanied by invertase which, unfortunately, degrades the saccharose present in sugar beet, or by lipase which adversely affects both the flavour and odour of soya-based products.

The present invention relates to a process for the production of α-galactosidase by culturing the mold *Penicillium duponti* in an aqueous medium containing at least one sugar with at least one αD-galactopyranosyl bond and collecting the mycelium thus obtained.

The culture medium used is preferably an optionally concentrated aqueous medium from the blanching of haricot beans. The culture medium may contain, per liter of water, from 6 to 20 g of dry material consisting of 30 to 40% by weight of sugars, 2 to 5% of total nitrogen, 12 to 20% of lipids and 13 to 18% of ash.

The sugars may consist of 30 to 40% of stachyose, 40 to 50% of saccharose, 7 to 9% of raffinose and from 1.5 to 3.5% of reducing sugars.

The pH-value of the medium is adjusted to between pH 6 and pH 7, and fermentation continued with stirring for 24 to 48 hours at a temperature in the range from 40° to 50°C.

The enzyme is synthesised in the cells of the microorganism. If the mycelium is separated from the culture medium by filtration for example, no trace of extracellular α-galactosidase can be found in the filtrate. It is for this reason that either the mycelium itself or an extract thereof may be collected as the enzymatic preparation. In the first case, it is of advantage to pulverise in a mortar the mycelium which has been separated from the medium and washed. In the second case, the mycelium may be homogenised in a buffer at pH 5.5 to pH 7.5, centrifuged and the supernatant phase collected. The α-galactosidasic activity of the supernatant phase is almost as great as that of the mycelium itself. Slight differences may be attributable to certain losses incurred during homogenisation. The mycelium as the enzyme may be maintained in lyophilised form and loses only a very small part of its properties as a result of this treatment.

It is possible by the process to prepare a biomass with a dry weight per liter of culture broth of from 2 to 3 g. If a unit (U) of α-galactosidasic activity is defined as the quantity of enzyme which releases 1 μg of reducing groups from a 0.05% stachyose solution in 30 minutes, the activity of the non-homogenised mycelium obtained by the process according to the invention may reach 45,000 U per g of dry mycelium, and the activity of the mycelium after homogenisation may reach 42,000 U per g of dry mycelium. This activity has numerous commercial uses. Conclusive results have been obtained in practical tests in which, on the one hand, the lyophilised enzyme was used for treating a soya milk and, on the other hand, the lyophilised mycelium was used for degrading the raffinose present in the juice of sugar beet.

The process according to the invention, and the properties of the product obtained by that process, are illustrated in the following Examples:

EXAMPLE 1

A water from the blanching of haricot beans (*Phaseolus vulgaris*) has the following composition in g/l:

| | |
|---|---|
| stachyose | 1.0 |
| raffinose | 0.2 |
| other sugars | 1.6 |
| total nitrogen | 0.4 |
| lipids | 1.7 |
| ash | 1.1 |

The pH-value of this water is adjusted to pH 6.5, after which the water is introduced into 2 liter flasks in quantities of 500 ml per flask. An inoculum of a strain of *Penicillium duponti* (*Talaromyces thermophilus*)

(ATCC 10518, CBS 23658) is introduced into the flasks. The inoculated flasks are agitated at 45°C in agitators turning at 120 rpm over a period of 24 hours. The culture broth is filtered by drawing it through ordinary sintered glass and the mycelium is collected, representing 2.7 g of dry material per liter of broth. A test on stachyose shows that the α-galactosidasic activity of the mycelium thus obtained amounts to 45,000 U per g of dry mycelium, one unit of activity (U) being defined as the quantity of enzyme which liberates 1 μg of reducing groups from a 0.05% stachyose solution in 30 minutes.

EXAMPLE 2

A water from the blanching of haricot beans has the following composition in g/l:

| | |
|---|---|
| stachyose | 1.2 |
| raffinose | 0.3 |
| other sugars | 2.1 |
| total nitrogen | 0.4 |
| lipids | 1.3 |
| ash | 1.8 |

A strain of *Penicillium duponti* (ATCC 10518) is cultured in this water under the same conditions as in Example 1. The mycelium collected after 48 hours of culture represents 2.9 g of dry material per liter of culture. After lyophilisation, the mycelium has an activity, tested on stachyose, of 39,000 U per g of dry material.

EXAMPLE 3

A water from the blanching of haricot beans having initially the same composition as in Example 2 is subjected to concentration, during which its volume is reduced by half. A strain of *Penicillium duponti* (ATCC 10518) is cultured in this medium which has twice the nutritive element concentration of the medium mentioned in Example 2. The fermentation conditions are identical with those of Example 1. The mycelium collected after 48 hours of culture represents 5.5 g of dry material per liter of culture. After lyophilisation, the mycelium has an activity, tested on stachyose, of 34,000 U per g of dry material.

EXAMPLE 4

A mycelium of *Penicillium duponti* (ATCC 10518) is prepared in the same way as in Example 1. This mycelium is homogenised in a 0.05 M acetate buffer (pH 6). It is then centrifuged at 23,000 rpm for 60 minutes. The supernatant phase is collected. The activity of the supernatant phase on the following substrates is tested:
1. saccharose
2. raffinose
3. stachyose
4. 4-nitrophenyl-β-D-glucopyranoside
5. 2-nitrophenyl-β-D-galactopyranoside
6. 2-nitrophenyl-α-D-galactopyranoside
7. azocoll
8. olive oil No activity whatever is detected with substrates 1, 5, 7 and 8. The supernatant phase does not contain any invertase, no β-galactosidase, no protease nor lipase. It contains an α-galactosidase and a β-glucosidase. The α-galactosidasic activity of the supernatant phase, tested on stachyose and defined as above, amounts to 42,000 U.

EXAMPLE 5

A mycelium of *Penicillium duponti* (ATCC 10518) is prepared in the same way as in Example 2. This mycelium is homogenised in a 0.05 M acetate buffer (pH 6). It is then centrifuged at 23,000 rpm for 30 minutes. The supernatant phase is collected. The α-galactosidasic activity of this supernatant phase, tested on sachyose, amounts to 40,000 U.

EXAMPLE 6

100 mg of the enzyme or supernatant phase prepared in the same way as in Example 4 and then lyophilised, are added to 500 ml of a soya milk containing 3.7% of stachyose. The enzymatic treatment is continued for 30 minutes at 55°C. After the treatment, the stachyose content of the soya milk is reduced to 40% with hardly any change in the taste of the milk.

EXAMPLE 7

1 g of mycelium produced in accordance with Example 1 is added to 200 ml of a sugar beet juice containing 22% of saccharose and 2% of raffinose. The enzymatic treatment is continued for 24 hours during which the degradation of the raffinose is observed. A percentage degradation of 40% is observed after approximately 1 hour, rising to 60% after about 2.5 hours, to around 80% after 4 hours, ultimately stabilising at around 85% after approximately 8 hours.

What is claimed is:
1. A process for the production of α-galactosidase by culturing the mold Penicillium duponti in an aqueous medium containing at least one sugar with at least one αD-galactopyranosyl bond, collecting the mycelium thus obtained and subjecting said collected mycelium to a step selected from the group consisting of lyophilization and treatment to liberate its intracellular content of α-galactosidase.
2. A process as claimed in claim 1, wherein the culture medium is an aqueous suspension from the blanching of haricot beans.
3. A process as claimed in claim 2, wherein the culture medium contains from 6 to 20 g of dry material per liter of water, the dry material containing from 30 to 40% by weight of sugars and from 2 to 5% of total nitrogen.
4. A process as claimed in claim 3, wherein the sugars consist of 30 to 40% of stachyose, 40 to 50% of saccharose, 7 to 9% of raffinose and 1.5 to 3.5% of reducing sugars.
5. A process as claimed in Claim 1, wherein the pH-value of the culture medium is adjusted to a value between 6 and 7.
6. A process as claimed in claim 1, wherein the medium is kept at a temperature of 40° to 50°C during fermentation.
7. A process as claimed in claim 1, wherein fermentation is continued for 24 to 48 hours.
8. A process as claimed in claim 1, wherein the mycelium collected is washed and then pulverised to liberate its intracellular content of α-galactosidase.
9. A process as claimed in claim 1, wherein the mycelium collected is homogenised in a buffer at a pH-value of from 5.5 to 7.5 to liberate its intracellular content of α-galactosidase, centrifuged and the supernatant phase collected.
10. The process of claim 1, wherein the mycelium are collected by separation from the culture medium.

* * * * *